United States Patent
Eischeid et al.

(10) Patent No.: US 7,241,201 B2
(45) Date of Patent: Jul. 10, 2007

(54) CMP PAD ANALYZER

(75) Inventors: Thomas J. Eischeid, State College, PA (US); Michael S. Biviano, State College, PA (US); Bradley S. Oaks, State College, PA (US); Raghu S. Srivatsa, State College, PA (US); Mahesh S. Bhardwaj, State College, PA (US)

(73) Assignee: The Ultran Group, Inc., State College, PA (US)

( * ) Notice: Subject to any disclaimer, the term of this patent is extended or adjusted under 35 U.S.C. 154(b) by 0 days.

(21) Appl. No.: 11/383,052

(22) Filed: May 12, 2006

(65) Prior Publication Data

US 2006/0258264 A1    Nov. 16, 2006

Related U.S. Application Data

(60) Provisional application No. 60/681,049, filed on May 16, 2005.

(51) Int. Cl.
*B24B 49/00* (2006.01)

(52) U.S. Cl. .................. 451/5; 451/8; 451/11
(58) Field of Classification Search .............. 451/5, 451/6, 8–11, 21, 41, 56, 59, 285–290, 910; 438/691–693
See application file for complete search history.

(56) References Cited

U.S. PATENT DOCUMENTS

| | | | |
|---|---|---|---|
| 6,186,864 B1 * | 2/2001 | Fisher et al. ................. | 451/6 |
| 6,684,704 B1 * | 2/2004 | Obeng ......................... | 73/602 |
| 7,033,246 B2 * | 4/2006 | Elledge et al. ................ | 451/5 |
| 2004/0043521 A1 * | 3/2004 | Elledge ........................ | 438/7 |

* cited by examiner

*Primary Examiner*—Dung Van Nguyen
(74) *Attorney, Agent, or Firm*—The Webb Law Firm

(57) ABSTRACT

An ultrasonic CMP polishing pad analyzer is disclosed. The analyzer provides a manufacturer or other user an ability to inspect a CMP polishing pad without removing the pad from the CMP machine by creating and displaying a topographical image of an in-service polishing pad. The analyzer includes an ultrasonic transducer and an analyzer body mounted to the CMP machine such that the ultrasonic transducer is positioned to receive reflected ultrasonic signals from a surface of the polishing pad.

18 Claims, 9 Drawing Sheets

CMP PAD ANALYZER

RELATED APPLICATIONS

This application claims priority to U.S. Provisional Application No. 60/681,049, filed May 16, 2005, the disclosure of which is hereby incorporated by reference in its entirety.

FIELD OF THE INVENTION

The present invention is directed to a system for analyzing polishing pads for chemical mechanical polishing machines and more particularly to an ultrasonic system to analyze the surface roughness and groove depth of the polishing pad without removing the pad from the platen surface of the polishing machine.

BACKGROUND OF THE INVENTION

Advances in electronic devices generally include reducing the size of the components that form integrated circuits. As semiconductor devices have become more highly integrated in recent years, circuit interconnections have become finer and distances between those circuit interconnections have become smaller. For example, in the case of photolithography, which can form interconnections smaller than 0.5 µm wide, surfaces on which pattern images are to be focused should be as flat as possible. Further, with smaller circuit components the value of each unit area of a semiconductor wafer becomes higher because the ability to use all of the wafer area for integrated circuit components improves. To properly form an integrated circuit that employs a much higher percentage of usable wafer area, contaminant particle counts on the semiconductor wafer surface must be reduced to very low levels. In order to clean a semiconductor wafer and remove unwanted particles, a process known as chemical mechanical polishing or chemical mechanical planarizing (hereinafter "CMP") has become popular.

The polishing is typically accomplished using a polishing pad attached to a platen surface of a CMP machine. A workpiece to be polished, such as a semiconductor wafer, is arranged in a manner such that a surface to be polished faces the polishing pad. The polishing pad and workpiece are independently rotated while an abrasive liquid or slurry is supplied onto the polishing pad. The workpiece is then pressed against the polishing pad at a predetermined pressure and the surface of the workpiece is polished to a flat mirror finish.

Polishing pads have a limited service life and become less effective over time. In turn, this results in inconsistent quality in the semiconductor wafers. As the polishing pad begins to lose its effectiveness, the semiconductor wafers polished later in the pad's life may be less smooth, possibly resulting in significant amounts of lost or unsaleable product. Thus, the polishing pads must be changed from time to time.

Current methods of determining the wear of a polishing pad, and thus whether the polishing pad is in need of replacement, are unsatisfactory. Analysis of the pad typically requires visual inspection. However, the pad usually cannot be visually inspected without removing the polishing pad from the CMP machine. Once removed, the polishing pad typically cannot be placed back on the machine, even if visual inspection determines some usable life remains. As a result, statistical analysis, based on experimental determination of pad wear over time under various operating conditions, is often used to make decisions about pad replacement. This is unsatisfactory for the reason, among others, that statistical analysis represents an average based on the wear of previous pads and is unable to account for any one particular pad or variations in quality or aberrant pads of inferior quality.

Furthermore, analysis of each polishing pad typically takes several hours or more and is often conducted by highly paid, highly skilled technicians whose time might be better used on other projects.

Another method of monitoring and analyzing polishing pad effectiveness is performing an analysis of the smoothness of the polished semiconductor wafer product. However, due to other steps required in wafer manufacture, this analysis is impractical until later in the manufacturing process. Thus, by the time defects in any one polishing pad are discovered and needed replacement is determined, the worn out pad may already have improperly polished many wafers remaining upstream of a suitable wafer analysis point, resulting in significant loss of product that must be discarded or recycled.

Conversely, using methods such as statistical analysis may also result in removing the polishing pad too soon, meaning that the full usable life of the polishing pad has not been obtained, resulting in the inefficient use of consumable materials. Thus, this also results in undesirable and uneconomic business practices.

What is needed is a system that can provide more efficient analysis of CMP polishing pads. What is also needed is a system that can analyze CMP polishing pads without removing the pad from the CMP machine.

SUMMARY OF THE INVENTION

The present invention meets these and other needs by providing an ultrasonic CMP pad analyzer that provides a manufacturer the ability to inspect a CMP polishing pad by creating and displaying a topographical image of an in-service polishing pad without removing the pad from the CMP machine. The analyzer periodically or continuously updates the image so that changes in the polishing pad surface can be viewed in real-time. This permits a user of the analyzer to maximize polishing pad life, reduce labor time lost to researching and inspecting polishing pads, and allows the manufacturer to monitor product quality more closely and thus provide a more consistent end product.

An ultrasonic CMP pad analyzer is disclosed. The analyzer comprises an ultrasonic transducer and an analyzer body. The analyzer body is configured to mount to a CMP machine having a polishing pad attached to a platen surface thereof and the ultrasonic transducer is positioned such that, when the analyzer body is mounted to the CMP machine, a sensor of the ultrasonic transducer is positioned to transmit ultrasonic signals toward and receive ultrasonic signals reflected from a surface of the polishing pad.

A method of analyzing a CMP pad is disclosed. The method comprises transmitting an ultrasonic wave from an ultrasonic transducer toward a surface of a polishing pad attached to a CMP machine and receiving ultrasonic signals reflected from the polishing pad surface, resolving the reflected ultrasonic signal from the surface of the polishing pad with the ultrasonic transducer, comparing the reflected signal with a predetermined base signal, calculating a topography of the polishing pad surface using the compared signals, displaying the topography of the polishing pad surface to a display device.

A system for creating an image of a CMP pad is disclosed. The system comprises an ultrasonic CMP polishing pad analyzer and a pad analysis station. The pad analyzer comprises an ultrasonic transducer and an analyzer body, wherein the analyzer body is configured to mount to a CMP machine having a polishing pad attached to a platen surface thereof, and wherein the ultrasonic transducer is positioned such that, when the analyzer body is mounted to the CMP machine, a sensor of the ultrasonic transducer is in a plane substantially parallel with a surface of the polishing pad. The pad analysis station comprises a processing machine, a memory device, a transmitter/receiver device, and a display screen. The processing machine is in electronic communication with the ultrasonic transducer and is configured to instruct the ultrasonic transducer, via the transmitter/receiver, to transmit ultrasonic waves toward the polishing pad surface. The processing machine is also configured to receive, via the transmitter/receiver, information contained in ultrasonic waves reflected by the polishing pad surface and is further configured to analyze the information contained in the received reflected ultrasonic waves to determine a topography of the polishing pad surface and display the determined topography as a visual image on the display screen.

One advantage of the invention is that an ultrasonic pad analyzer in accordance with exemplary embodiments of the invention allows polishing pads for a CMP machine to be analyzed without removing the pad from the machine.

Another advantage of the invention is that the analysis can be visually displayed in realtime so that a person viewing the display can inspect the polishing pad via the display and identify aberrations or wear patterns that indicate the need for a polishing pad to be replaced.

Yet another advantage of the invention is that maximum polishing pad life may be obtained and avoids the need to resort to statistical analysis, decreasing losses resulting from discarding polishing pads having useful life as well as from discarding inferior finished product produced by untimely identification and replacement of a worn-out polishing pad.

Still another advantage of the invention is that the time for determining whether a polishing pad needs replaced is greatly reduced, restoring productivity of skilled workers lost to timely alternative inspection methods.

Another advantage of the invention is that a manufacturer of silicon wafers, or other products that include CMP as part of the manufacturing process, can produce a product of more consistent quality and avoid variations caused by inconsistent polishing pad quality.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

For clarity, it has been attempted to use like numerals where like parts are referenced with respect to more than one drawing.

DETAILED DESCRIPTION OF THE INVENTION

Figure 1:
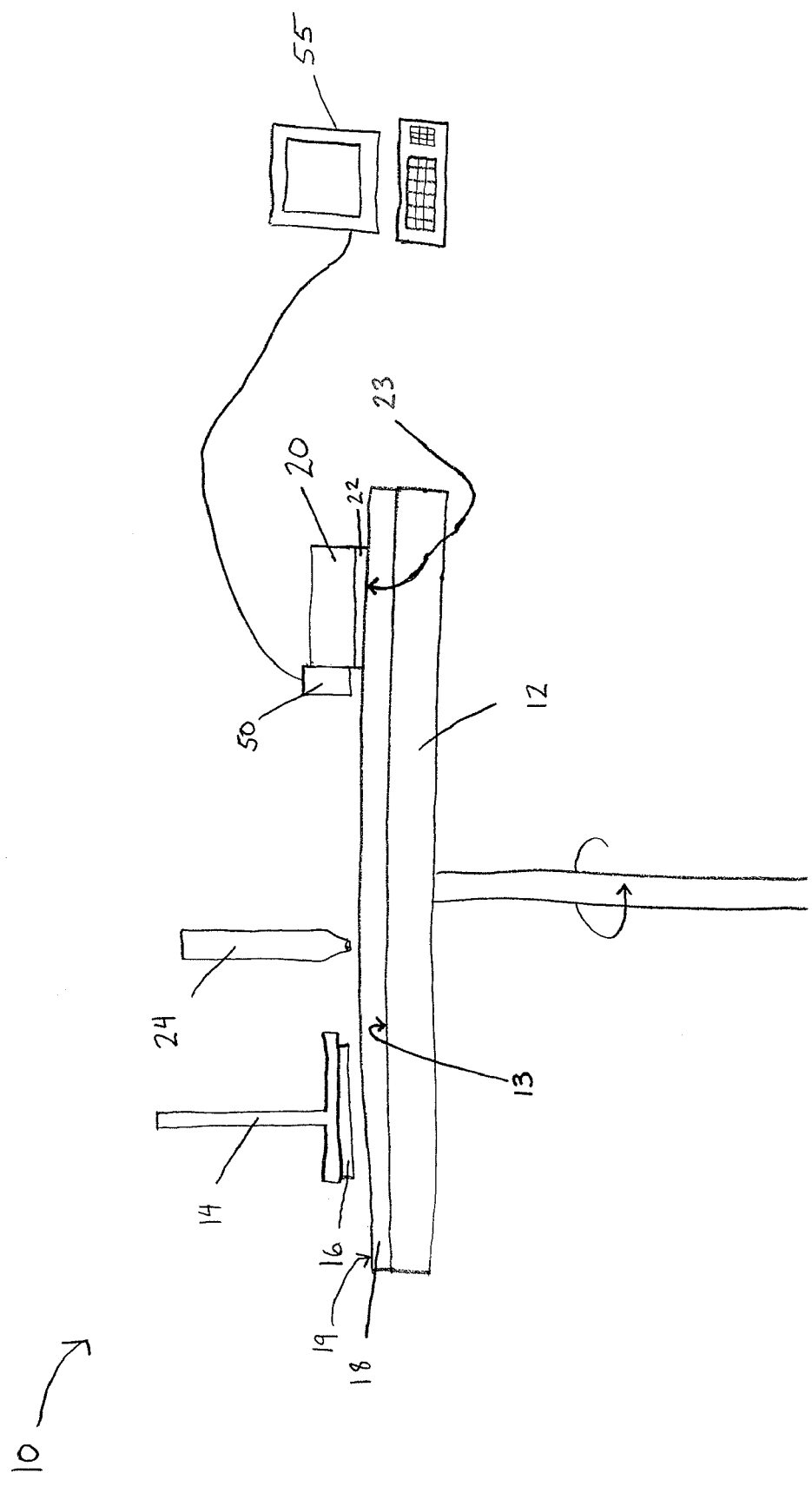
FIG. 1 illustrates a CMP machine having an ultrasonic pad analyzer in accordance with an exemplary embodiment of the invention.

Referring to FIG. 1, a chemical mechanical polishing (CMP) machine 10 includes a rotatable table 12 having a platen surface 13 on which a polishing pad 18 having a polishing pad surface 19 is mounted. A workpiece 16, such as a semiconductor wafer to be polished, is positioned above the polishing pad 18, such as through the use of a holder 14 or other similar device.

The polishing pad 18 and the holder 14 may be independently rotated at pre-determined rates and the workpiece 16 may be lowered against the polishing pad surface 19 by applying a variable load to the holder 14, depending on the amount of polishing desired for a particular workpiece. A liquid is distributed over the polishing pad surface 19, such as through a slurry feeder 24 positioned over the polishing pad 18. The liquid occupies the space between the workpiece 16 and the pad 18 during operation. Typically, the liquid contains a colloidal suspension of abrasive particles, such as alumina or silica, as well as specific chemicals chosen for polishing. The holder 14 is brought down on the pad with a specific load as both the holder 14 and pad 18 are rotated. Material is removed from the workpiece 16 surface by a combined action of chemical dissolution and abrasion, all in accordance with well-known CMP machine operation.

Also in accordance with well-known CMP operation the CMP machine 10 may include a conditioning arm 20 having a conditioning pad 22 attached thereto. The conditioning pad 22 includes a conditioning surface 23 for contacting and conditioning the polishing pad surface 19. The conditioning pad 22 typically includes fine diamond or other fine grit bonded to the conditioning surface 23 of a suitable pad material, which pad 22 is then attached to a rotating disc on the conditioning arm 20. The conditioning pad 22 traverses the polishing pad 18, renewing the polishing pad surface 19 and restoring polishing pad performance. More specifically, the conditioning arm 20 can be pivoted such that the conditioning pad 22 is disposed over different portions of the polishing pad 18 such that the conditioning surface 23 of the conditioning pad 22 is in contact with different portions of the polishing pad surface 19. This enhances the effectiveness of the polishing pad 18 for use in polishing the workpiece 16. However, conditioning removes still more material from the polishing pad surface 19 so that over time the polishing pad 18 is slowly ground away, thus shortening the polishing pad's usable life.

According to exemplary embodiments of the invention, the CMP machine 10 includes an ultrasonic pad analyzer 50. The ultrasonic pad analyzer 50 provides a user or other observer an ability to inspect the efficacy of a particular polishing pad 18 while still attached to the polishing machine 10. This facilitates changing the polishing pad 18 when it actually needs replaced and avoids basing pad replacement determinations on methods that do not adequately account for aberrant or uneven wear patterns of any single polishing pad.

Preferably, the ultrasonic pad analyzer 50 permits real-time analysis of the polishing pad surface 19, such as by generating and displaying a topographical or relief diagram or map of the polishing pad surface 19 on a display screen associated with a pad analysis station 55 in electronic communication with the ultrasonic pad analyzer 50. A user can monitor the displayed image and thus inspect the pad 18 to determine when the wear of the pad is approaching a predetermined minimum thickness or variations in thickness, for example, that suggest the polishing pad 18 has reached the end of its useful life and should be replaced. The pad analysis station 55 may further be configured to automatically detect and alert a user that the polishing pad 18 should be replaced based on a predetermined minimum thickness, predetermined unacceptable variations in thickness, or other any other predetermined indicia associated with the polishing pad 18 approaching or having reached the end of its useful life.

Figure 2:
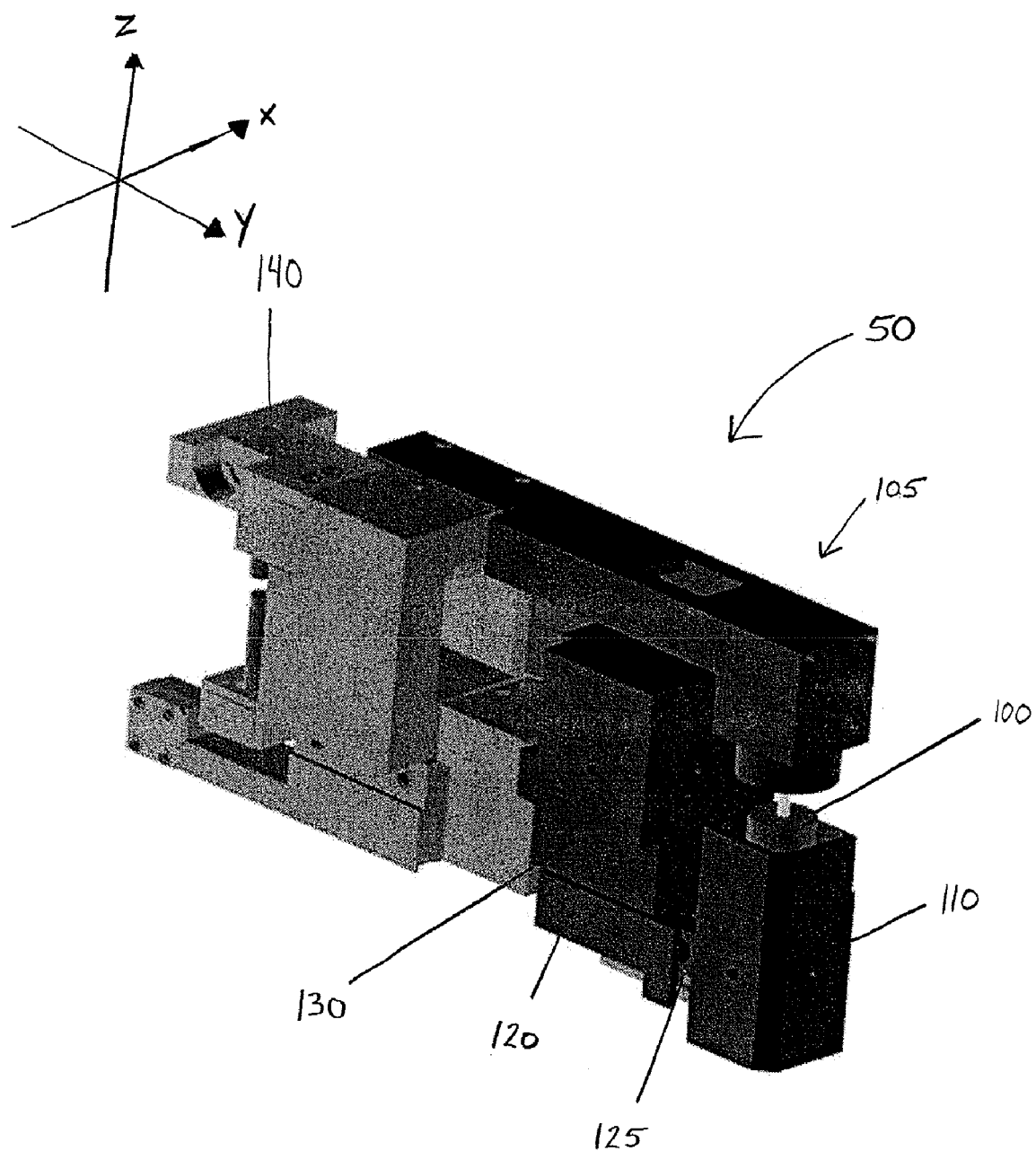
FIG. 2 is a perspective view of an ultrasonic pad analyzer in accordance with an exemplary embodiment of the invention.
Figure 8:
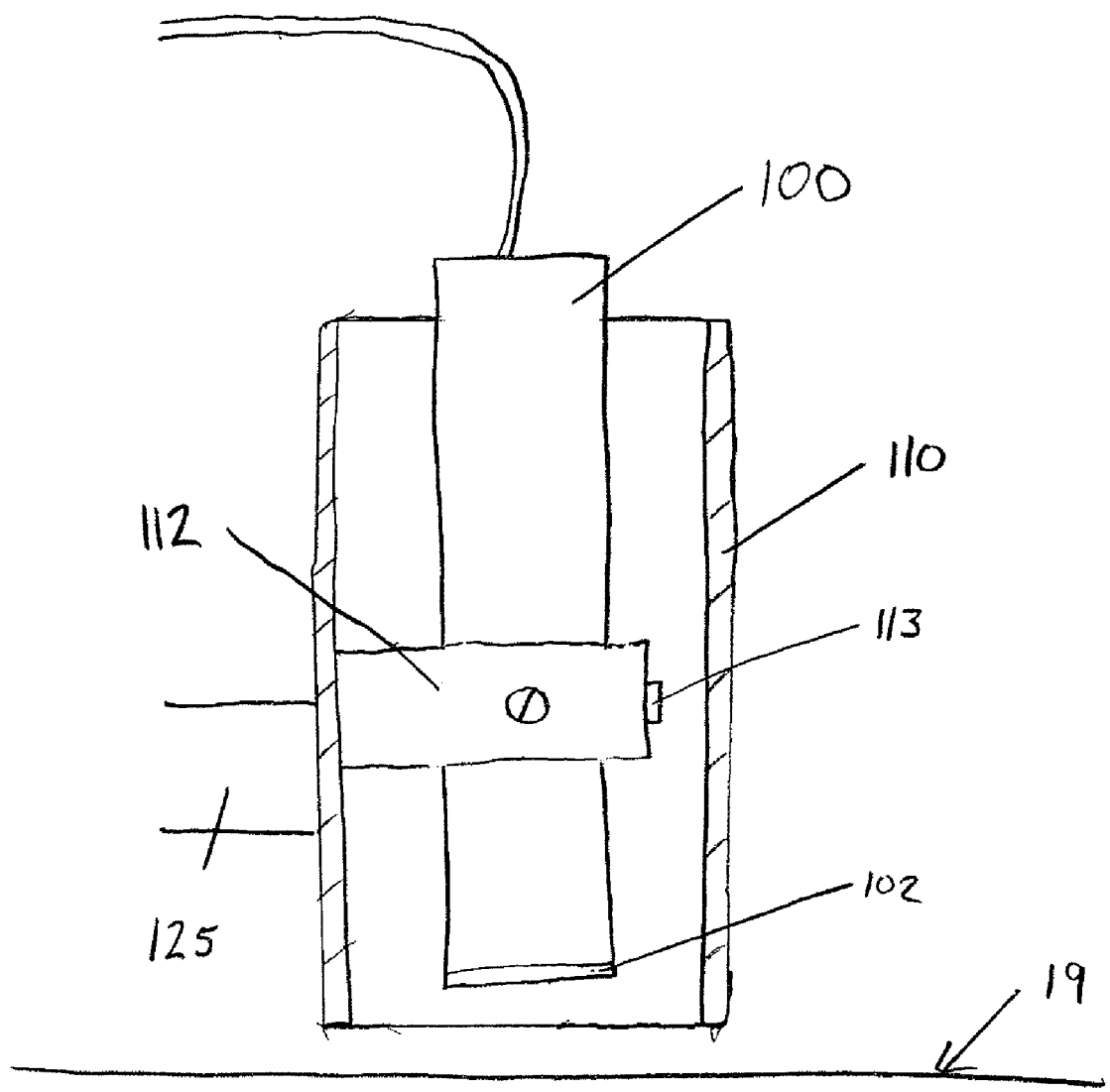
FIG. 8 is a sectional view of the water chamber illustrating the transducer disposed therein.

Referring now to FIG. 2, the ultrasonic pad analyzer 50 comprises an ultrasonic transducer 100 and an analyzer body 105. The analyzer body 105 includes a water chamber 110 in which the transducer 100 is at least partially disposed. The ultrasonic transducer is preferably an immersion transducer, meaning that the working medium between a sensor lens 102 (shown in FIG. 8) of the transducer 100 and the test material, i.e. the polishing pad surface 19, through which transmitted and reflected ultrasonic signals travel, is a liquid. Typically, a transducer 100 is selected having a frequency or range of frequencies between about 2 MHz and about 150 MHz. The particular frequency to be used and thus the transducer selected may depend on a number of user specific factors such as the porosity of the polishing pad 18 and the desired resolution of the data obtained.

It will be appreciated that although exemplary embodiments of the invention are discussed with respect to a transducer 100 illustrated as a single device, the transducer for use with exemplary embodiments also encompasses multiple transducer devices arranged in a "pitch-catch" (transmit-receive) configuration, as is known to those of ordinary skill in the art, in which one transducer is typically responsible only for transmitting ultrasonic pulses while a separate transducer is dedicated to receiving the reflection signals.

Figure 3:
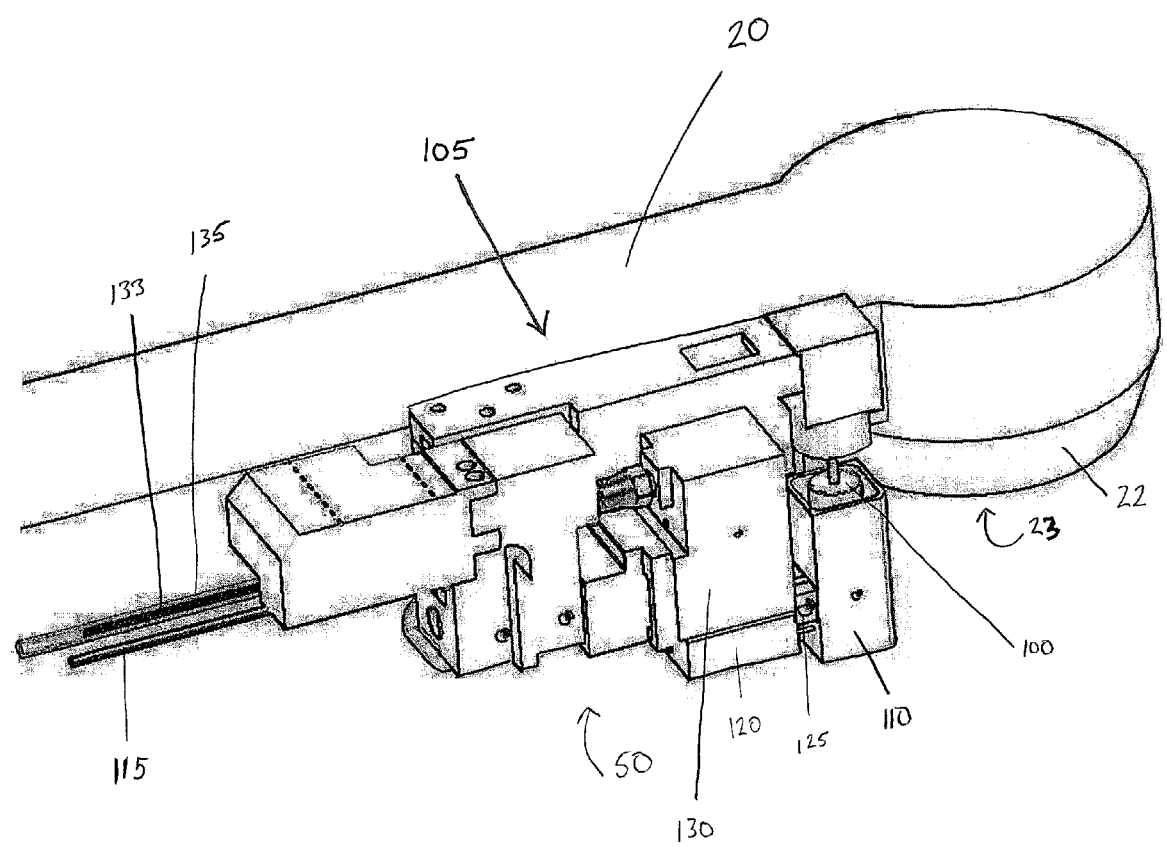
FIG. 3 is a perspective view of an ultrasonic pad analyzer mounted to a conditioning arm of a CMP machine.

Fluctuations in liquid level can result in a destabilized ultrasonic signal transmitted and received by the transducer 100, resulting in undesirable operation and poor data results. The liquid medium preferably completely fills all space between the transducer sensor lens 102 and the polishing pad surface 19. To avoid the potential problem caused by liquid fluctuation and to ensure that the liquid medium completely fills the space through which the pulsed ultrasonic waves travel, the transducer 100 is at least partially disposed in the water chamber 110 so that the sensor lens 102 is completely submerged to ensure that the immersion transducer 100 is operating in a sufficient amount of liquid. Additional liquid, typically in the form of water, is supplied to the transducer via an external water line 115, as better seen in FIG. 3. More typically, the additionally supplied water is de-ionized ("D.I.") water.

Figure 7:
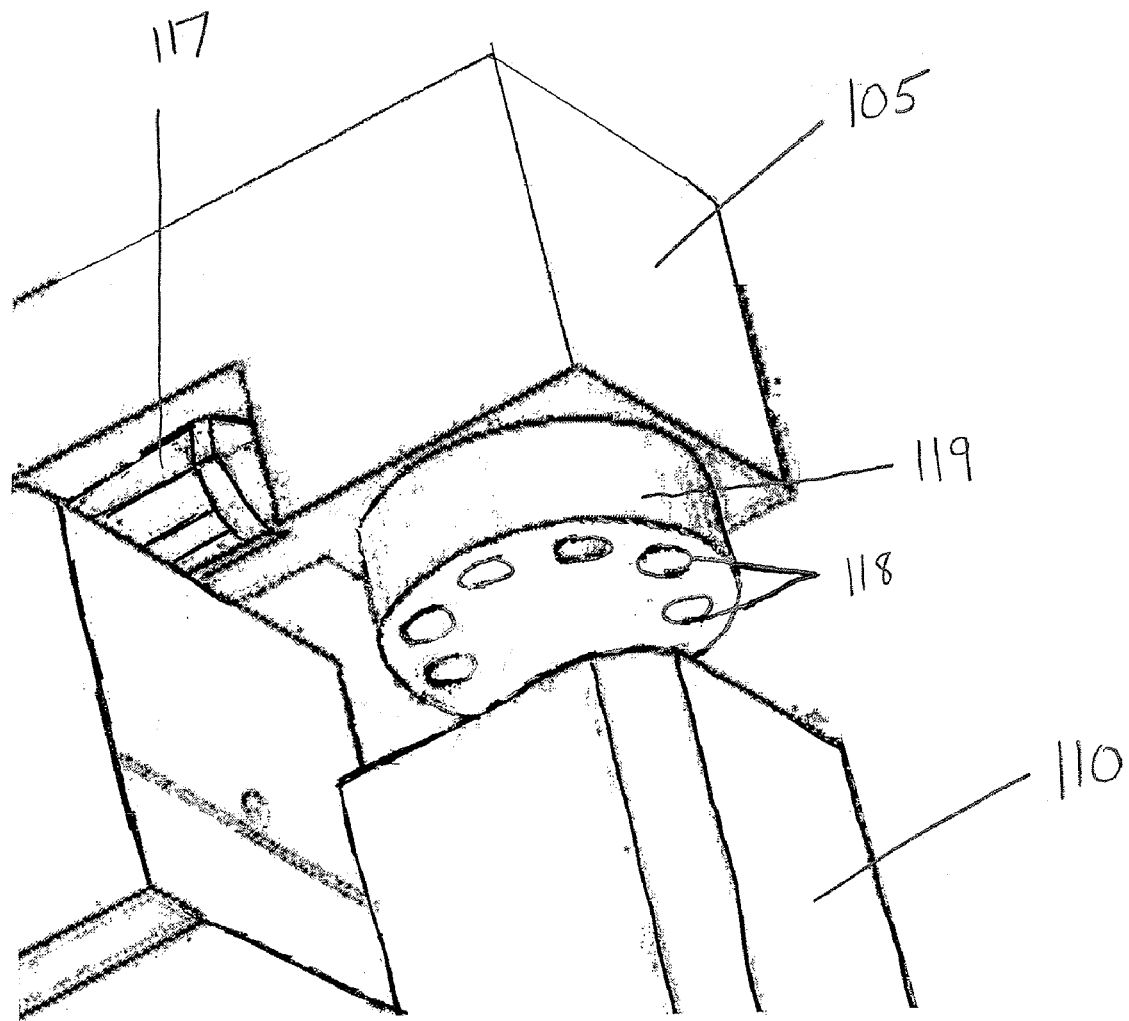
FIG. 7 is a perspective view of the underside of the water outlet portion of the analyzer body.

The water line 115 passes from an external water source, to which it is connected on one end, to an outlet near the water chamber on the other end. As better seen with reference to FIG. 7, the water line 115 directs water to a water outlet portion 119 of the analyzer body 105, which may be facilitated by a water line fitting 117 that mates with the analyzer body 105. The water outlet portion 119 contains one or more water outlets 118, which may be arranged in a shower-head fashion for even distribution of water.

The water outlet(s) 118 direct water into the water chamber 110 such that it flows over, and is evenly distributed around, the transducer 100. The water then merges with the water or slurry composition supplied by the slurry feeder 24 to the rotating polishing pad 18. This additional flow of water helps create a plenum of liquid that assists in stabilizing the ultrasonic signal during operation of the analyzer 50.

Depending on the type of workpiece 16 being polished on a CMP machine 10, in some circumstances a rougher, more porous polishing pad 18 may be used, while in other circumstances, a smoother, less porous pad 18 may be used instead. As a result, it may be desirable to provide multiple transducers interchangeable with the analyzer 50 so that a particular transducer can be matched with a particular type or style of polishing pad with which it is well suited based on the pad's roughness and porosity. Two transducers may be provided in which the transducers are interchangeable depending on whether the polishing pad is rough or smooth.

A smooth surface reflects an ultrasonic signal more strongly than a rough surface. A rougher surface results in more scattering of the ultrasonic signal and thus produces a received or returned signal with lower amplitude. As used herein, "rough" pads refer to pads that are characterized by surfaces which substantially scatter frequencies above 50 MHz. "Smooth" pads do not result in as much scattering of the incident ultrasound wave and therefore allowing the opportunity for evaluation at higher frequencies. Thus, a transducer of lower frequency is preferable for more porous, rougher pads while a higher frequency transducer may be used on less porous, finer pads.

The ultrasonic pad analyzer 50 can be positioned at any location such that the ultrasonic transducer 100 is positioned over the polishing pad 18 and preferably should be mounted in a manner that does not unduly obstruct movement of the conditioning arm 20 or other components important to the polishing operations of the CMP machine 10. Again referring to FIG. 3, the analyzer 50 may be conveniently mounted on an interior side of the conditioning arm 20 of the CMP machine 10, i.e., the side of the conditioning arm 20 closest to the axis of rotation of the table 12 and polishing pad 18, although the analyzer 50 may be modified to mount to any type of CMP machine 10.

The ultrasonic pad analyzer 50 may be constructed such that it is capable of numerous mechanical adjustments for use in a variety of different CMP applications. According to one embodiment of the invention, the ultrasonic pad analyzer 50 includes a means for aligning the ultrasonic transducer 100 so that the sensor lens 102 is better positioned to detect ultrasonic signals transmitted by the transducer 100 and reflected back by the polishing pad surface 19. Typically, the ultrasonic pad analyzer is positioned so that the sensor lens 102 is in a plane substantially parallel with the polishing pad surface 19. According to another embodiment of the invention, the analyzer 50 includes means for adjusting the transducer 100 in the z-direction to adjust the distance between the transducer 100 and the polishing pad surface 19. As best seen in the sectional view of the water chamber 110 shown in FIG. 8, the transducer 100 is secured to the water chamber 110 so that adjustments made to the analyzer body 105 (FIGS. 2 and 3) result in corresponding adjustments to the transducer 100. By way of example only, the transducer 100 may be secured by a bracket 112, machined in or otherwise connected to the water chamber 110, and one or more set screws 113.

Alignment and positioning of the ultrasonic transducer 100 with respect to the plane of the polishing pad surface 19 is accomplished by rotating portions of the analyzer body 105 with respect to other portions of the analyzer body 105. More specifically, portions of the analyzer body 105 are adjusted to arc about either one or both of the x and y axes. The adjustments may provide the transducer with a range of motion of up to about 10 degrees from normal in any direction. The adjustments may be in increments as small as one minute or smaller, to permit nearly any position within a cone of about 20 degrees thus providing better resolution of the reflected signal.

Figure 4:
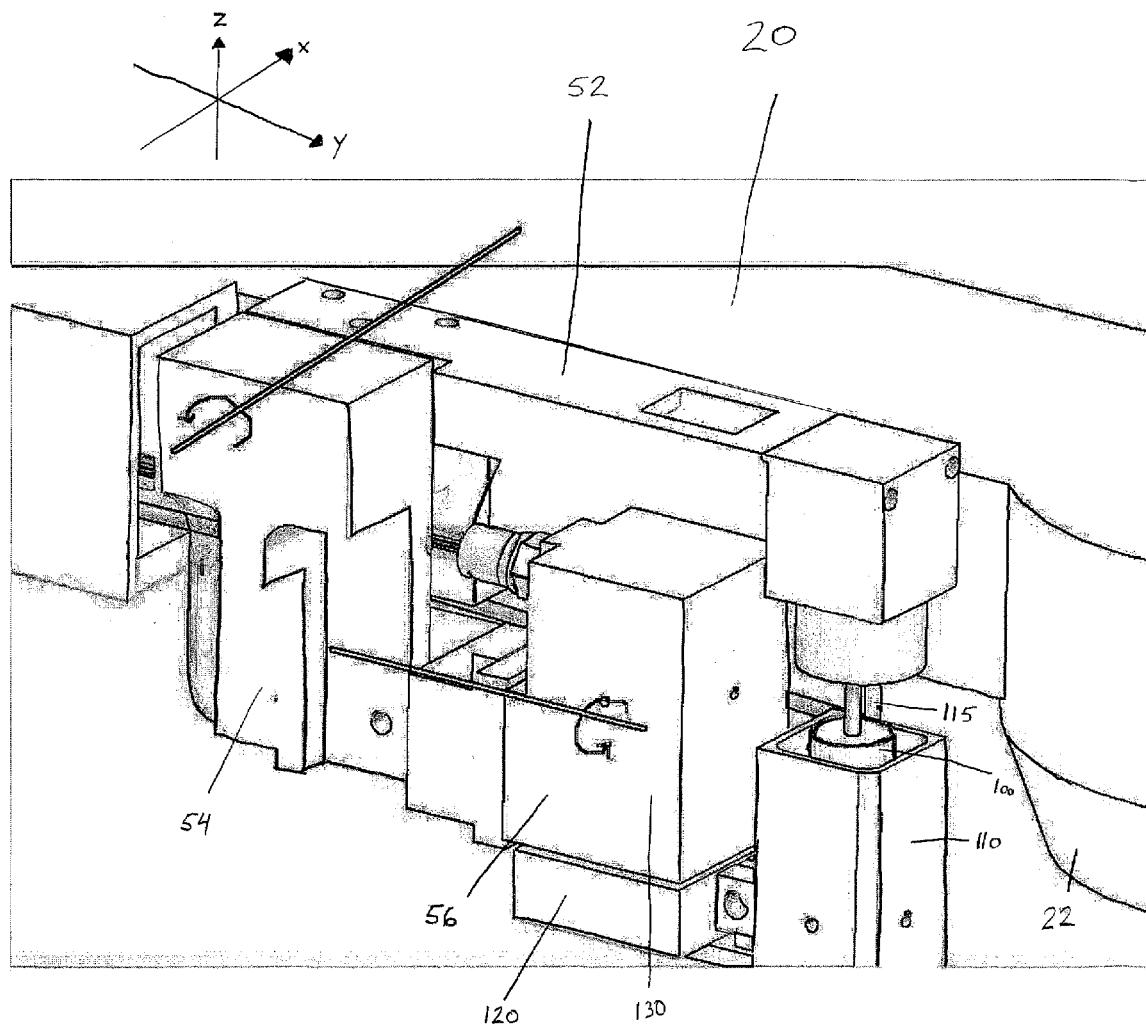
FIG. 4 is a perspective view of a portion of an ultrasonic pad analyzer illustrating axial alignment of the analyzer according to an exemplary embodiment of the invention.

The rotation about each of the x and y axis may be accomplished in any suitable manner. As illustrated in FIG. 4, a mounting portion 52 of the analyzer 50 is rigidly attached to the conditioning arm 20. The mounting portion 52 is connected to a first alignment portion 54 via a first alignment axle (not shown) that is oriented parallel with the x-axis. Likewise, the mounting portion 52 is connected to a second alignment portion 56 via a second alignment axle (also not shown). The alignment axles may be sturdy rods constructed of any suitable material and are typically driven by one or more gears rotated manually, or automatically, such as through instructions provided by a computer.

Alignment typically occurs over a specified target that strongly reflects ultrasonic signals. Any material that provides an adequate signal with respect to amplitude and frequency response can be used as the target. Typically, target materials possess an acoustic impedance much higher than water. A polished stainless steel surface, such as the platen surface underlying the polishing pad is an example of a suitable target. The primary purpose of the target is to provide a reference signal to determine if the transducer needs to be realigned. The target may be located at a home position of the conditioning arm 20, in which the conditioning arm is pivoted away from the polishing pad 18.

Once the analyzer 50 has been properly aligned with the polishing pad surface 19 to achieve a maximum reflected value of the ultrasonic signal from the transducer 100, the value of the reflected signal is recorded in a memory of the pad analysis station 55 as a base signal for later use in the analysis of the polishing pad 18 as described in more detail below. The analyzer is preferably properly aligned upon initial installation and typically does not need subsequent realignment except for minor adjustments which may be desirable at predetermined maintenance intervals.

It should be appreciated that variations may exist in the machining tolerances of the CMP machine 10 and/or those of the ultrasonic pad analyzer 50. As a result, according to another exemplary embodiment of the invention, in addition to rotation about the x and y axes, the first and second alignment portions 54, 56 may also be adjusted in an axial manner to compensate for any such machining changes to further align and position the transducer 100 at a desired location with respect to the polishing pad 18.

According to another embodiment of the invention, the ultrasonic pad analyzer 50 is mechanically configured to permit movement of the ultrasonic transducer 100 along the z-axis. Z-axis movement permits the transducer 100 to be adjusted to a desired distance from the alignment target and/or the polishing pad surface 19. In some cases, a worn polishing pad 18 may be replaced with one of a different thickness. This in turn results in a change in the distance between the sensor lens 102 of the transducer 100 and the polishing pad surface 19 that may require readjustment for proper performance when the CMP machine 10 and analyzer 50 are returned to operation. The typical height between the water chamber 110 and the polishing pad surface 19 is about 2 mm to about 3 mm, although smaller and larger heights could also be used without serious adverse effects. Referring again to FIG. 8, the transducer 100 may optionally be secured to the water chamber 110 in such a manner that the transducer 100 is further recessed from the polishing pad surface 19, such that the transducer 100 is about 0 mm to about 2 mm farther from the polishing pad surface 19 than the water chamber, or a total of about 2 mm to about 5 mm above the polishing pad surface 19.

Adjusting the analyzer 50 in the z direction also permits the transducer 100 to rise out of the way when not in use. For example, the transducer may need an adjustment in the z direction in order for a technician to access the polishing pad 18 for replacement or at other times when the transducer 100 it is not physically accessible for a manual adjustment. Furthermore, due to the intricate adjustments often necessary to obtain precise and accurate readings, the z-axis adjustment preferably occurs via a computer-controlled connection. According to a preferred embodiment of the invention, the z-axis motion is accomplished by an electrical linear actuator with a small step size, typically on the order of about 10 μm, although larger and smaller step sizes are acceptable.

The environment surrounding the pad analyzer 50 is typically harsh, due to vibration of the CMP machine 10 and the nature of the composition of the liquid slurry, both of which are typically present during operation. As a result, working mechanical parts, such as the alignment axles, and electrical devices, such as the linear actuator, may be protected from the surrounding environment by housing them within the analyzer body 105. More specifically, the linear actuator may be contained within an actuator housing 120, while a motor used to drive the actuator and optionally the alignment axles, may be contained within a motor housing 130.

The actuator housing 120 is connected to the water chamber 110 via a connecting arm 125, such that when the linear actuator is activated, the actuator housing 120 extends toward or away from the motor housing 130 in the z-direction, causing the water chamber 110, and thus the transducer 100, to also raise or lower.

In addition to the external water line 115 discussed previously, other cables and lines from a source external to the CMP machine 10 may be connected to the pad analyzer 50. Exemplary cables may include a cable to carry power to the motor in the motor housing 130 and a cable connected between the transducer 100 and the pad analysis station 55 to and from which information regarding ultrasonic signals is transmitted and received.

In some cases, the relative sizes of the CMP machine 10 and the polishing pad 18 may present spatial restraints on the movement of various working parts of the CMP machine 10, such as the holder 14 or conditioning arm 20 for example, that may be further constrained by the use of the ultrasonic pad analyzer 50 positioned over the polishing pad 18. To reduce the impact of any spatial restraints introduced by the ultrasonic pad analyzer 50, the pad analyzer 50 may be configured to facilitate management of external lines so that buckling or bending of the lines does not interfere with or get in the way of the CMP machine's polishing operations. Preferably, any external lines pass through one or more channels provided in the analyzer body 105 that permit direct delivery of those lines to their intended destination. Cables carrying electronic signals may comprise a single cable bundle 133 that passes from an external source to a suitable connection point on the pad analyzer 50 via a conduit 135.

Figure 5:
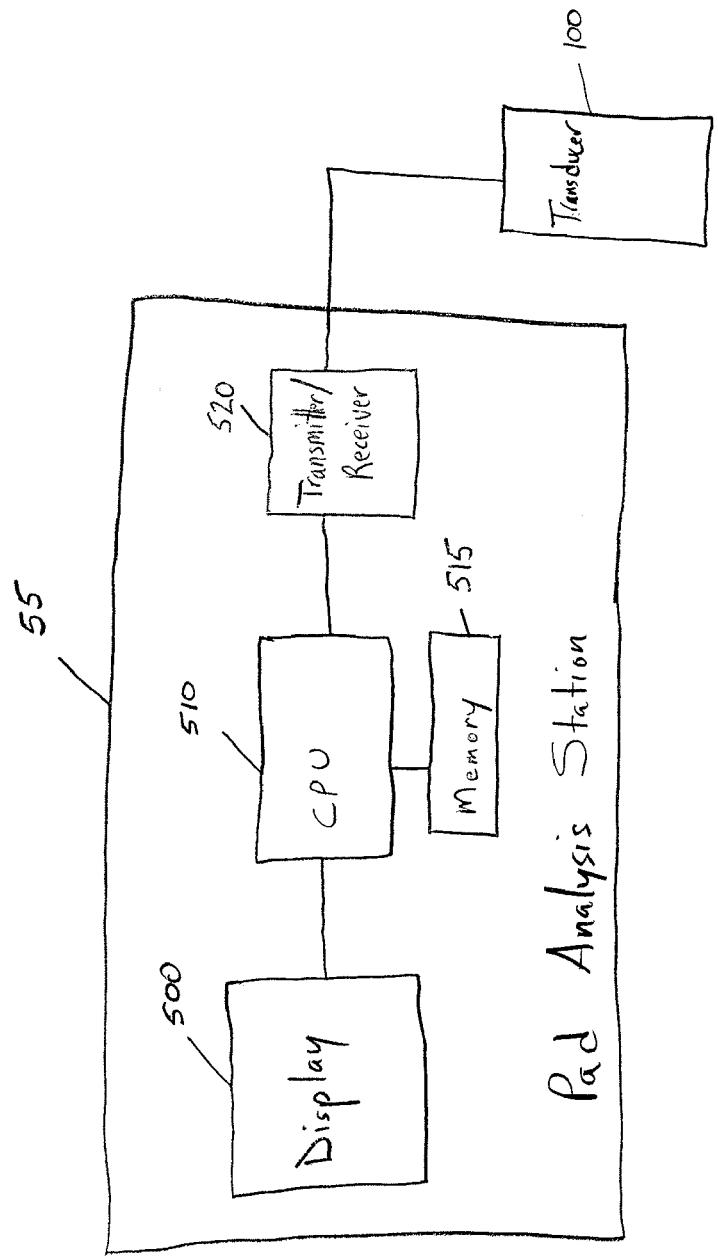
FIG. 5 is a block diagram of a polishing pad analysis station in communication with the transducer of the ultrasonic pad analyzer in accordance with exemplary embodiments of the invention.

Referring now to FIG. 5, the transducer 100 is in electronic communication with a pad analysis station 55, which is typically a CPU or other processing machine 510 having software loaded thereon that, when executed, causes a pulse in a transmitter/receiver device 520 to send ultrasonic signals from the transducer 100. Upon detection of any reflected signals from the polishing pad surface 19, the detected signal is passed backed to the pad analysis station 55. Accordingly, after the transducer has been properly aligned and has been adjusted to the proper height along the z-axis, the pad analyzer 50 can be used during CMP machine polishing operations to send and receive ultrasonic signals consistent with basic principles of ultrasonic detection that are then passed to the pad analysis station 55 for use in analyzing the wear of the polishing pad 18 and changes in the polishing pad surface 19 for display to a user via a display screen 500. The pad analysis station further comprises a memory device 515 for storing the base signal and may store any other data for use by the comparison and other analysis conducted by the processing machine 510. The memory device may be any suitable device for the electronic storage of information.

The transducer 100 may be wired directly to the pad analysis station 55 using a single cable. Although the use of multiple cables and/or additional electrical and mechanical connections is not precluded, introducing such devices may degrade the transmitted/received signal to an unsatisfactory level.

Figure 6:
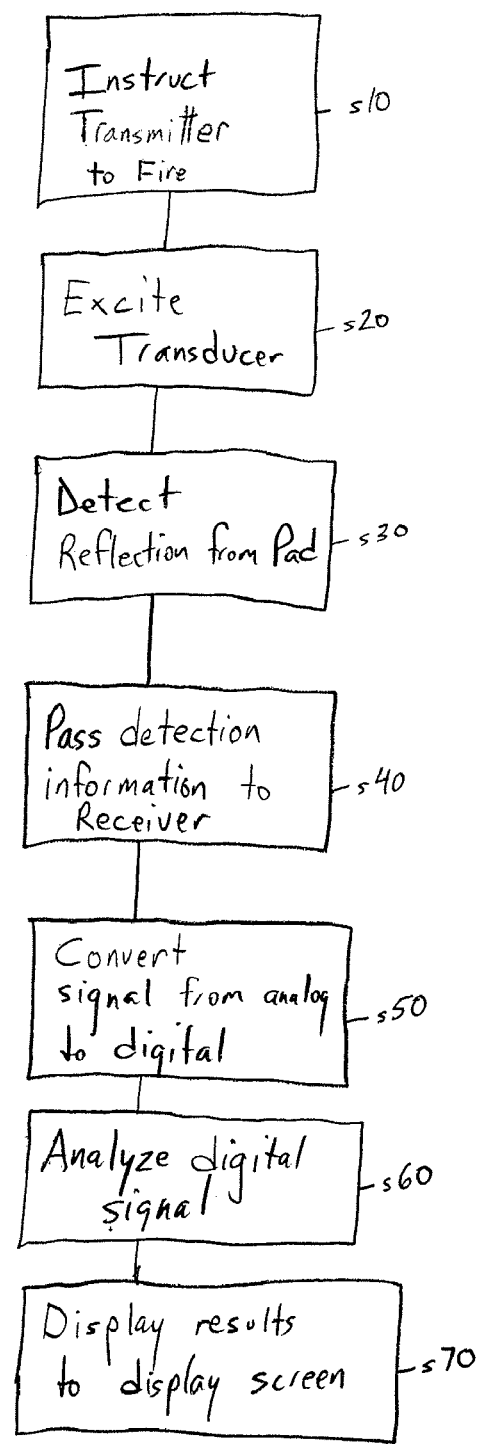
FIG. 6 is a flow chart illustrating a method for analyzing a polishing pad according to an exemplary embodiment of the invention.

According to yet another embodiment of the invention, a method for analyzing a polishing pad using an ultrasonic pad analyzer 50 is provided as illustrated in FIG. 6. At step s10, the processor 510 at the pad analysis station 55 instructs the transmitter 520 to send an ultrasonic signal. The transducer 100 operates by converting an electrical pulse into a mechanical pulse by vibrating the sensor or crystal, thereby transmitting a mechanical pulse at ultrasonic frequency through the polishing pad. A mechanical signal striking the sensor or crystal from the polishing pad causes the sensor to mechanically vibrate, which in turn is converted to an electrical pulse.

In response to an instruction, the transmitter 520 sends an electric signal that excites the transducer 100 at step s20, causing the transducer 100 to transmit an ultrasonic pulse. The ultrasonic pulse strikes the polishing pad surface 19 and reflects back to the sensor lens on the transducer 100. The transducer 100 detects the reflected ultrasonic signal at s30, thus receiving information about the topography of the polishing pad surface 19 in the form of a reflected ultrasonic pulse by determining the amount of time it takes for the transmitted signal to return and by determining the amplitude of the reflected pulse.

The received information is passed to a receiver 520 at step s40. The receiver may be the same device as the transmitter, configured to operate in a dual role as both a transmitter and a receiver as is known in the art. As discussed, the reflected ultrasonic signal detected by the transducer 100 is in the form of mechanical waves, i.e., an analog form. Thus, at step s50, an analog-to-digital converter, which may further be part of the transmitter/receiver device 520, converts the received analog signal into digital information usable by the processing machine 5 10.

At step s60, the converted digital signal is analyzed by the processing machine 510 according to one or more algorithms depending on the type of information being requested by a user, which is then displayed to the pad analysis station display screen 500 at step s70. As the polishing pad 18 is used, the polishing pad surface 19 changes as parts of the pad are slowly worn away. By comparing the amplitude of and time to receive detected signals reflected from the polishing pad surface 19 to that of the previously recorded maximum determined during initial alignment, the processing machine is able to calculate changes in the distance from the transducer 100 to the polishing pad surface 19. Using this distance information, the processing machine 510 compiles a topography of the polishing pad surface 19 that can be displayed to a user in the form of a relief map.

Figure 9:
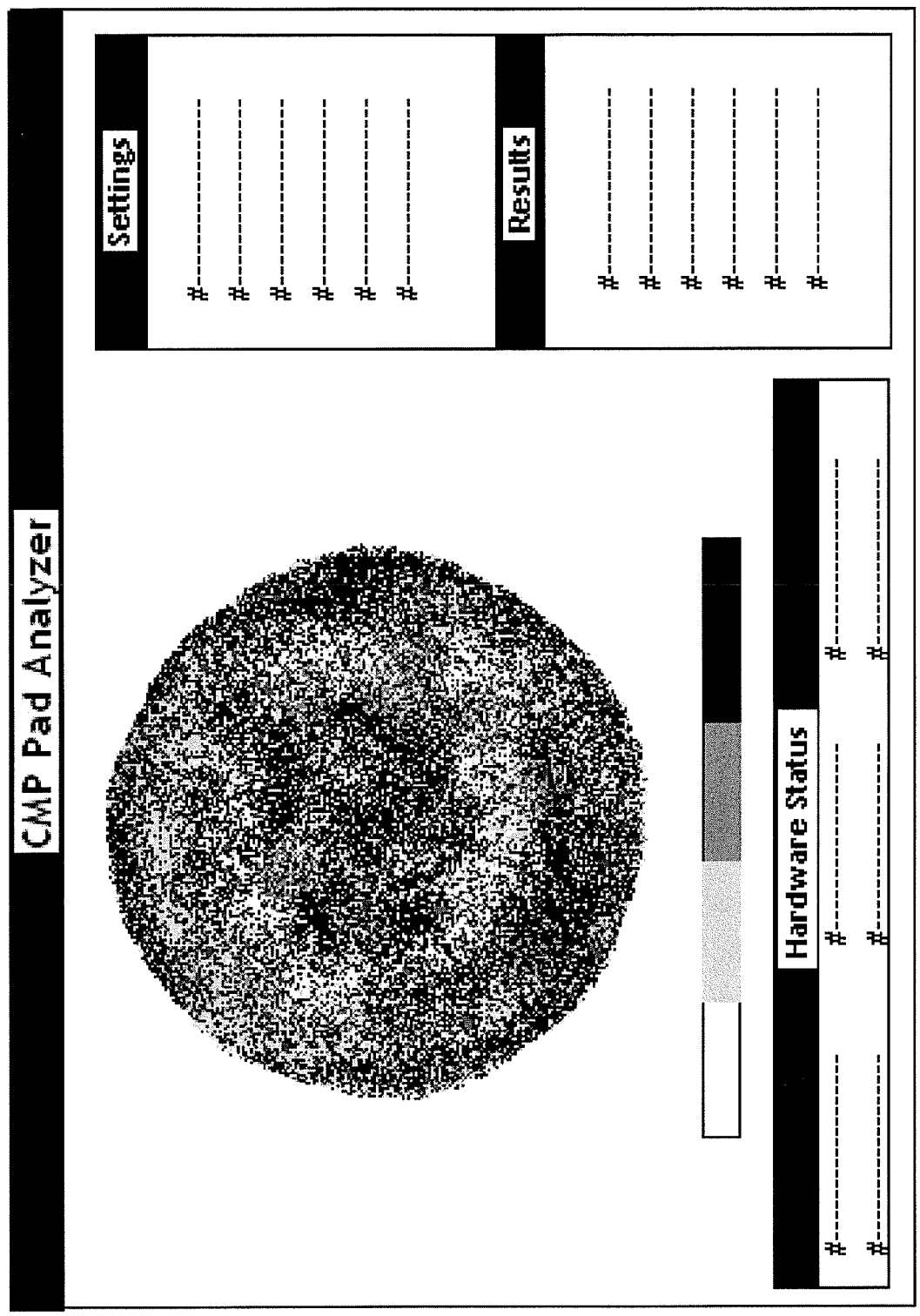
FIG. 9 is an exemplary screen shot illustrating one manner in which the pad analysis station may display the results obtained using the ultrasonic pad analyzer.

The relief map may be visually inspected by a user to determine whether the information provided by the pad analyzer 50 suggests a polishing pad 18 is in need of replacement. Elevations of the pad surface may advantageously be color coded for a user to more easily inspect pad wear when viewing the display screen 500. Additionally, or in combination, the processing machine 510 may be provided with one or more predetermined logical rules, which if met, result in warnings displayed to the user to automatically alert the user that a polishing pad 18 is in need of replacement. For example, the pad analysis station 55 may be programmed in such a manner that if the processor 510 calculates that the polishing pad 18 is worn down to a pre-determined minimum thickness, a warning will be displayed to the user alerting the user that the polishing pad is in need of replacement. By way of further example, pitting and uneven or other unacceptable wear patterns may develop that are evidenced, for example, by extreme changes in elevation over a portion of the polishing pad service. If these changes are outside of a predetermined tolerance, for example greater than a predetermined slope, a warning may again be displayed to the user identifying the need for a change in polishing pads. A screen shot showing one example of how the pad analysis station may display the relief map of the polishing pad is shown in FIG. 9.

As a result, maximum polishing pad life can be achieved by analysis of the actual polishing pad 18 installed on the CMP machine 10, without resorting to statistical analysis and without the risk that a polishing pad will be removed with useful life remaining or that a polishing pad of aberrant quality that wears out earlier than expected will result in significant amounts of lost product.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An ultrasonic chemical mechanical polishing ("CMP") machine polishing pad analyzer comprising:
    an ultrasonic transducer; and
    an analyzer body, wherein the analyzer body is configured to mount to a CMP machine having a polishing pad attached to a platen surface thereof, and wherein the ultrasonic transducer is positioned such that, when the analyzer body is mounted to the CMP machine, the ultrasonic transducer is positioned to transmit and receive reflected ultrasonic signals from a surface of the polishing pad to analyzer a pre-selected feature of the pad further comprising means for aligning the sensor of the ultrasonic transducer in a plane substantially parallel with the polishing pad surface, wherein the means for aligning the ultrasonic transducer in a plane parallel with the polishing pad comprises a device for rotating the transducer with respect to the x-axis and a device for rotating the transducer with respect to the y-axis.

2. The analyzer of claim 1, further comprising means for adjusting the ultrasonic transducer along the z-axis to modify a distance between the ultrasonic transducer and the polishing pad.

3. The analyzer of claim 2, wherein the means for adjusting the ultrasonic transducer along the z-axis comprises a linear actuator.

4. The analyzer of claim 3, wherein the linear actuator is contained within an actuator housing portion of the analyzer body.

5. The analyzer of claim 1, wherein the analyzer body is mounted to a conditioning arm of the CMP machine.

6. A method for analyzing a CMP polishing pad surface comprising:
   transmitting an ultrasonic wave from an ultrasonic transducer through a water chamber toward a surface of a polishing pad attached to a CMP machine;
   receiving a reflected ultrasonic signal from the surface of the polishing pad with the ultrasonic transducer;
   analyzing the received reflected signal;
   comparing the received reflected signal with a predetermined base signal;
   calculating a topography of the polishing pad surface using the compared signals; and
   displaying the topography of the polishing pad surface to a display device.

7. The method of claim 6, wherein the step of comparing further comprises:
   receiving the reflected ultrasonic signals in analog form from the ultrasonic transducer; and
   converting the received analog signals to digital information.

8. The method of claim 6, wherein the base signal is a previously determined signal corresponding to transmitting an ultrasonic signal from the ultrasonic transducer toward a predetermined target and receiving, at the ultrasonic transducer, a reflected ultrasonic signal from the surface of the predetermined target.

9. The method of claim 6, wherein calculating a topography comprises determining a distance from the ultrasonic transducer to the polishing pad surface at a plurality of points on the polishing pad surface.

10. The method of claim 9, further comprising using the determined distance from the ultrasonic transducer to the polishing pad surface for at least one point on the polishing pad surface to calculate a polishing pad thickness at the at least one point.

11. The method of claim 10, further comprising comparing the calculated polishing pad thickness to a pre-determined minimum polishing pad thickness.

12. The method of claim 11, further comprising alerting a user if the calculated polishing pad thickness is equal to or less than the pre-determined minimum polishing pad thickness.

13. The method of claim 6, further comprising displaying the topography of the polishing pad surface to the display device in substantially real-time.

14. A system for creating an image of a CMP polishing pad comprising:
   an ultrasonic CMP polishing pad analyzer comprising:
   an ultrasonic transducer; and
   an analyzer body, wherein the analyzer body is configured to mount to a CMP machine having a polishing pad attached to a platen surface thereof, wherein the analyzer body comprises a water chamber, wherein the ultrasonic transducer is at least partially disposed in the water chamber, and wherein the ultrasonic transducer is positioned such that, when the analyzer body is mounted to the CMP machine, the ultrasonic transducer is in a plane substantially parallel with a surface of the polishing pad; and
   a pad analysis station comprising:
   a processing machine;
   a memory device;
   a transmitter/receiver device; and
   a display screen, wherein the processing machine is in electronic communication with the ultrasonic transducer and wherein the processing machine is configured to instruct the ultrasonic transducer, via the transmitter/receiver, to transmit ultrasonic waves toward the polishing pad surface, wherein the processing machine is configured to receive, via the transmitter/receiver, information contained in ultrasonic waves reflected by the polishing pad surface, and wherein the processing machine is configured to analyze the information contained in the received reflected ultrasonic waves to determine a topography of the polishing pad surface and display the determined topography as a visual image on the display screen.

15. The system of claim 14, wherein the processing machine is configured to analyze the information contained in the sensed reflected ultrasonic waves to determine a topography of the polishing pad surface and display the determined topography as a visual image on the display screen in real-time.

16. The system of claim 14, wherein the ultrasonic pad analyzer comprises means for aligning the ultrasonic transducer in the plane substantially parallel with the polishing pad and means for adjusting the ultrasonic transducer along the z-axis.

17. An ultrasonic chemical mechanical polishing ("CMP") machine polishing pad analyzer comprising:
   an ultrasonic transducer; and
   an analyzer body, wherein the analyzer body is configured to mount to a CMP machine having a polishing pad attached to a platen surface thereof, and wherein the ultrasonic transducer is positioned such that, when the analyzer body is mounted to the CMP machine, the ultrasonic transducer is positioned to transmit and receive reflected ultrasonic signals from a surface of the polishing pad to analyze a pre-selected feature of the pad wherein the analyzer body comprises a water chamber, wherein the ultrasonic transducer is at least partially disposed in the water chamber.

18. The analyzer of claim 17, further comprising an external water line configured to deliver water to the water chamber from a source external to the analyzer body.

* * * * *